US010422916B2

(12) United States Patent
Zhang et al.

(10) Patent No.: US 10,422,916 B2
(45) Date of Patent: Sep. 24, 2019

(54) METHODS AND SYSTEMS FOR DETERMINING BULK DENSITY, POROSITY, AND PORE SIZE DISTRIBUTION OF SUBSURFACE FORMATIONS

(71) Applicant: Saudi Arabian Oil Company, Dhahran (SA)

(72) Inventors: Jilin Zhang, Cypress, TX (US); Stacey Marie Althaus, Houston, TX (US); Jin-Hong Chen, Katy, TX (US)

(73) Assignee: Saudi Arabian Oil Company, Dhahran (SA)

(*) Notice: Subject to any disclaimer, the term of this patent is extended or adjusted under 35 U.S.C. 154(b) by 133 days.

(21) Appl. No.: 15/673,996

(22) Filed: Aug. 10, 2017

(65) Prior Publication Data
US 2019/0049616 A1    Feb. 14, 2019

(51) Int. Cl.
*G01N 15/08*    (2006.01)
*G01N 24/08*    (2006.01)
(Continued)

(52) U.S. Cl.
CPC ............. *G01V 3/32* (2013.01); *G01N 15/088* (2013.01); *G01N 24/081* (2013.01); *G01N 24/082* (2013.01); *G01R 33/448* (2013.01)

(58) Field of Classification Search
CPC ...... G01N 15/00; G01N 15/08; G01N 15/088; G01N 24/00; G01N 24/08; G01N 24/081; G01N 24/082; G01R 33/448; G01V 3/32
See application file for complete search history.

(56) References Cited

U.S. PATENT DOCUMENTS 3,409,092 A    11/1968  Doremus
3,494,188 A    2/1970   Boatman, Jr.
(Continued)

FOREIGN PATENT DOCUMENTS

CN    107677587 A  *  2/2018    ............. G01N 15/08
GB    2542406 A        3/2017
(Continued)

OTHER PUBLICATIONS

International Search Report and Written Opinion for corresponding PCT/US2017/051527 dated Oct. 26, 2017; pp. 1-12.
(Continued)

*Primary Examiner* — Nguyen Q. Ha
(74) *Attorney, Agent, or Firm* — Bracewell LLP; Constance G. Rhebergen; Vivek P. Shankam (57) ABSTRACT

Herein methods and systems for determining matrix or grain density of a subsurface formation are described. This includes measuring in-air mass of a fluid-saturated sample of the subsurface formation, wherein the in-air mass comprises mass of matrix or grains of the sample, mass of a fluid surrounding the sample, and mass of the fluid inside the sample. The volume of the fluid inside the sample, $V_\varphi$, and volume of the fluid surrounding the sample, $V_{sur}$, are determined using nuclear magnetic resonance (NMR). The fluid-saturated sample can then be submerged in a predetermined volume of a weighing fluid and mass of the fluid-saturated sample without the surrounding fluid in the weighing fluid, $m_f$ is measured. Using the measured and determined values one can determine the volume of the sample without the surrounding fluid, $V_c$, the bulk density of the fluid-saturated sample without the surrounding fluid, $\rho_b$, the volume of the matrix, $V_m$, and the matrix or grain density of the subsurface formation, $\rho_m$.

9 Claims, 11 Drawing Sheets

(51) Int. Cl.
*G01V 3/32* (2006.01)
*G01R 33/44* (2006.01)

(56) References Cited

U.S. PATENT DOCUMENTS

| | | | |
|---|---|---|---|
| 6,453,727 | B1 | 9/2002 | Lenormand et al. |
| 6,765,380 | B2 | 7/2004 | Freedman |
| 6,958,604 | B2 | 10/2005 | An et al. |
| 7,082,812 | B2 | 8/2006 | Lenormand et al. |
| 7,131,317 | B2 | 11/2006 | Lenormand et al. |
| 7,388,373 | B2 | 6/2008 | Lenormand et al. |
| 7,924,001 | B2 | 4/2011 | Minh |
| 8,686,724 | B2 | 4/2014 | Mitchell et al. |
| 8,727,145 | B2 | 5/2014 | Zollondz et al. |
| 8,857,243 | B2 | 10/2014 | Valenza, II et al. |
| 8,967,249 | B2 | 3/2015 | Akkurt et al. |
| 9,176,251 | B2 | 11/2015 | Singer et al. |
| 2003/0094946 | A1 | 5/2003 | Galford et al. |
| 2006/0272812 | A1 | 12/2006 | Yu et al. |
| 2013/0113480 | A1 | 5/2013 | Viswanathan et al. |
| 2013/0234703 | A1 | 9/2013 | Chen et al. |
| 2013/0259190 | A1* | 10/2013 | Walls ............... G01N 23/22 378/9 |
| 2013/0282288 | A1 | 10/2013 | Quinn et al. |
| 2015/0219782 | A1 | 8/2015 | Kadayam |
| 2015/0240633 | A1 | 8/2015 | Akkurt et al. |
| 2016/0061803 | A1 | 3/2016 | Hadj-Sassi et al. |

FOREIGN PATENT DOCUMENTS

| | | | | |
|---|---|---|---|---|
| RU | 2654315 C1 | * | 5/2018 | ............ G01N 15/08 |
| WO | 2011133859 A1 | | 10/2011 | |

OTHER PUBLICATIONS

Boatman, W. A., Measuring and Using Shale Density to Aid in Drilling W Measuring and Using Shale Density to Aid in Drilling Wells in High-pressure Areas. American Petroleum Institute; https://www.onepetro.org/conference-paper/API-67-121, 1967.

Research Report—HRC-RET-201509-0xx; Method for Measurement of Hydrocarbon Content in Shale Gas Reservoir; Jinhong Chen, Stacey M. Althaus, and Hui-Hai Liu.

Anonymous, "Porosity", AAPG Wiki, 2014, pp. 1-9.

Franklin, "Suggested Methods for Determining Water Content, Porosity, Density, Absorption and Related Properties and Swelling and Slake-Durability Index Properties" International Society for Rock Mechanics, 1977, pp. 14, ISRM.

International Search Report and Written Opinion for related PCT application PCT/US2018/045931 dated Nov. 27, 2018; pp. 1-16.

* cited by examiner

METHODS AND SYSTEMS FOR DETERMINING BULK DENSITY, POROSITY, AND PORE SIZE DISTRIBUTION OF SUBSURFACE FORMATIONS

TECHNICAL FIELD

Embodiments relate to reservoir evaluation. More specifically, example embodiments relate to methods and systems for determining bulk density, porosity, and pore size distribution of subsurface formations. These methods and systems utilize a combination of (Nuclear Magnetic Resonance) NMR and gravimetric techniques.

BACKGROUND

Bulk density is one of the most important parameters in reservoir evaluation. It is widely used for estimation of reserves of hydrocarbons in reservoirs. Traditionally, well logs and core measurements are the two approaches to obtain key petrophysical parameters for reservoir evaluation and description. These measurements are expensive and many times they require extra rig time, which is also very expensive.

For example, bulk density can be measured in real time with logging while drilling (LWD) density log or can be measured using wireline (WL) density log. Both use a gamma ray source and measure the attenuated gamma ray coming to the detector after interacting with the formation. Generally speaking, the LWD density measurement represents the bulk density of the rock with the formation fluids in the pore space, whereas the WL density measures the bulk density of the rock with invaded fluids; for low permeable unconventional rocks, the difference should be minimal. Bulk density can be precisely measured using core plugs when they are available.

Obtaining accurate petrophysical parameters from drill cuttings is beneficial and desirable for at least two reasons. First, drill cuttings are readily available from any drilled well and thus does not add extra rig time or extra cost to the operation. Second, measurement can be done at the wellsite and offers data for real-time operational decisions, such as drilling and the succeeding hydraulic fracturing.

However, it is a challenge to measure the volume of the cutting accurately as it is hard to remove the fluid on the surface of the cutting. The traditional sample preparation method uses a damp paper towel to remove the excess fluid from the surface, and due to the irregular shape of the surface features, the validity of the total removal of the surface fluid is always questionable. Moreover, if the paper towel is too dry, the fluid within the cutting sample can be lost due to capillary force.

SUMMARY

Example embodiments disclosed herein relate to improved methods and systems for determining bulk density, porosity, and pore size distribution of subsurface formations.

One example embodiment is a method for determining matrix or grain density of a subsurface formation. The method includes measuring an in-air mass of a fluid-saturated sample of the subsurface formation, wherein the in-air mass includes mass of the matrix or grains of the sample, mass of a fluid surrounding the sample, and mass of the fluid inside the sample. The in-air mass of the fluid-saturated sample, $m_s$, may be given by the formula $$m_s = \rho_m + (V_\phi + V_{sur})\rho_l$$

where $\rho_m$ is a density of the matrix of the subsurface formation, $\rho_l$ is a density of the fluid inside and surrounding the sample, $V_m$ is a volume of the matrix, $V_\phi$ is a volume of the fluid inside the sample, and $V_{sur}$ is a volume of the fluid surrounding the sample. The method also includes separately determining volume of the fluid inside the sample, $V_\phi$, and volume of the fluid surrounding the sample, $V_{sur}$, using nuclear magnetic resonance (NMR). The method may further include placing the sample in a predetermined volume of a weighing fluid, and measuring mass of the fluid-saturated sample in the weighing fluid. The mass of the fluid-saturated sample without the surrounding fluid in the weighing fluid, $M_f$, may be given by the formula $$m_f = V_m \rho_m + V_\phi \rho_l - V_c \rho_f$$

where $\rho_f$ is the density of the weighing fluid. The method may further include determining a volume of the fluid-saturated sample without the surrounding fluid, $V_c$, using the formula $$V_c = (m_s - m_f - V_{sur}\rho_l)/\rho_f$$

The method may also include determining a bulk density of the fluid-saturated sample without the surrounding fluid, $\rho_b$, using the formula $$\rho_b = \frac{V_m \rho_m + V_\phi \rho_l}{m_s - m_f - V_{sur}\rho_f} \rho_f.$$

The method may further include determining the volume of the matrix, $V_m$, using the formula $$V_m = (m_s - m_f - V_{sur}\rho_f)/\rho_f - V_\phi.$$

The method may also include determining the matrix or grain density of the subsurface formation, $\rho_m$, using the formula $$\rho_m = \frac{m_s - (V_\phi + V_{sur})\rho_f}{(m_s - m_f - V_{sur}\rho_f)/\rho_f - V_\phi}.$$

Another example embodiment relates to computer programs stored in computer readable media. The non-transitory computer-readable media may have, for example, computer executable instructions that trigger the computer to perform the operation of receiving in-air mass of a fluid-saturated sample of the subsurface formation, wherein the in-air mass includes mass of the matrix or grains of the sample, mass of a fluid surrounding the sample, and mass of the fluid inside the sample. The in-air mass of the fluid-saturated sample, $m_s$, may be given by the formula $$m_s = V_m \rho_m + (V_\phi + V_{sur})\rho_l$$

where $\rho_m$ is a density of the matrix of the subsurface formation, $\rho_l$ is a density of the fluid inside and surrounding the sample, $V_m$ is a volume of the matrix, $V_\phi$ is a volume of the fluid inside the sample, and $V_{sur}$ is a volume of the fluid surrounding the sample. The computer executable instructions may also trigger the computer to determine the volume of the fluid inside the sample, $V_\phi$, and volume of the fluid surrounding the sample, $V_{sur}$, from NMR measurements. The computer executable instructions may also trigger the computer to receive the mass of the fluid-saturated sample in a weighing fluid. The mass of the fluid-saturated sample without the surrounding fluid in the weighing fluid, $m_f$, may be given by the formula $$m_f = V_m \rho_m + V_\phi \rho_l - V_c \rho_f$$

where $\rho_f$ is the density of the weighing fluid. The computer executable instructions may also trigger the computer to calculate a volume of the fluid-saturated sample without the surrounding fluid, $V_c$, using the formula $$V_c = (m_s - m_f - V_{sur}\rho_l)/\rho_f$$

The computer executable instructions may further trigger the computer to calculate a bulk density of the fluid-saturated sample without the surrounding fluid, $\rho_b$, using the formula $$\rho_b = \frac{V_m \rho_m + V_\phi \rho_l}{m_s - m_f - V_{sur}\rho_f} \rho_f.$$

The computer executable instructions may further trigger the computer to calculate the volume of the matrix, $V_m$, using the formula $$V_m = (m_s - m_f - V_{sur}\rho_f)/\rho_f - V_\phi.$$

The computer executable instructions may further trigger the computer to calculate the matrix or grain density of the subsurface formation, $\rho_m$, using the formula $$\rho_m = \frac{m_s - (V_\phi + V_{sur})\rho_f}{(m_s - m_f - V_{sur}\rho_f)/\rho_f - V_\phi}.$$

Another example embodiment is a system for determining matrix or grain density of a subsurface formation. The system may include a fluid-saturated sample of the subsurface formation, and a weighing balance, which may be configured to receive the fluid-saturated sample and output the in-air mass and in-fluid mass of the sample. The system may also include a computer having one or more processors and a non-transitory computer readable medium, which may include computer executable instructions that when executed by the one or more processors, trigger the computer to fetch in-air mass of the fluid-saturated sample of the subsurface formation from the weighing scale. The in-air mass may include mass of the matrix or grains of the sample, mass of a fluid surrounding the sample, and mass of the fluid inside the sample. The in-air mass of the fluid-saturated sample, $m_s$, may be given by the formula $$m_s = V_m \rho_m + (V_\phi + V_{sur})\rho_l$$

where $\rho_m$ is a density of the matrix of the subsurface formation, $\rho_l$ is a density of the fluid inside and surrounding the sample, $V_m$ is a volume of the matrix, $V_\phi$ is a volume of the fluid inside the sample, and $V_{sur}$ is a volume of the fluid surrounding the sample. The system may also include an NMR, which may be operably connected to the computer and configured to determine the volume of the fluid inside the sample, $V_\phi$, and volume of the fluid surrounding the sample, $V_{sur}$, using NMR. The computer may be configured to receive the volume of the fluid inside the sample, $V_\phi$, and volume of the fluid surrounding the sample, $V_{sur}$, from the NMR, and the mass of the fluid-saturated sample in a weighing fluid from the weighing scale. The mass of the fluid-saturated sample without the surrounding fluid in the weighing fluid, $m_f$, may be given by the formula $$m_f = V_m \rho_m + V_\phi \rho_l - V_c \rho_f$$

where $\rho_f$ is the density of the weighing fluid. The computer executable instructions may also trigger the computer to determine a volume of the fluid-saturated sample without the surrounding fluid, $V_c$, using the formula $$V_c = (m_s - m_f - V_{sur}\rho_l)/\rho_f$$

The computer executable instructions may further trigger the computer to determine a bulk density of the fluid-saturated sample without the surrounding fluid, $\rho_b$, using the formula $$\rho_b = \frac{V_m \rho_m + V_\phi \rho_l}{m_s - m_f - V_{sur}\rho_f} \rho_f.$$

The computer executable instructions may further trigger the computer to determine the volume of the matrix, $V_m$, using the formula $$V_m = (m_s - m_f - V_{sur}\rho_f)/\rho_f - V_\phi.$$

The computer executable instructions may further trigger the computer to determine the matrix or grain density of the subsurface formation, $\rho_m$, using the formula $$\rho_m = \frac{m_s - (V_\phi + V_{sur})\rho_f}{(m_s - m_f - V_{sur}\rho_f)/\rho_f - V_\phi}.$$

DETAILED DESCRIPTION

Example embodiments disclosed propose a method to measure and analyze drill cuttings using a combination of nuclear magnetic resonance (NMR) measurements and mass measurements in-air and in-fluid to obtain multiple key petrophysical parameters accurately with little sample preparation. Example embodiments present a new and accurate method to measure the bulk density using saturated drill cuttings, which are readily available for any drilled hydrocarbon well. The method combines NMR and gravimetric techniques, and the results include bulk density, grain density, porosity, and pore-size distribution of the drill cuttings.

Figure 1:
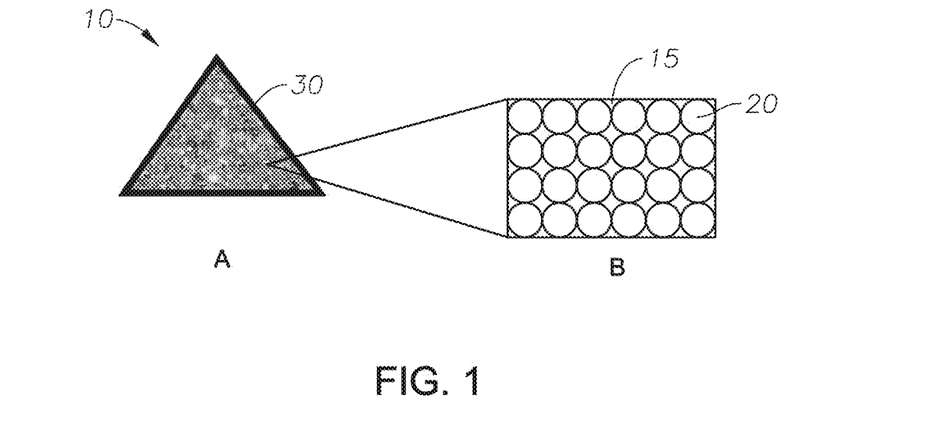
FIG. 1 illustrates an example sample or drill cutting of a subsurface formation, according to one example embodiment of the disclosure.

Turning now to the figures, FIG. 1 illustrates a sample 10, such as a drill cutting of a subsurface formation, such as from a hydrocarbon reservoir. In an exemplary method, the first step is to collect drill cuttings 10 that are representative of the subsurface formation. The next step is to size-sort as to eliminate particles of large size, which are normally from caving, and to eliminate particles of too small a size, which may have circulated multiple times through the up-hole and down-hole cycles with the drilling mud. In some embodiments, at least one dimension of the fluid-saturated sample may be about 0.5 mm to 3 mm. These limits, however, can be adjusted according to the specific formation and the bits used for drilling.

Additionally, the collected cuttings may be washed using sufficient fluid such that it minimizes the impact of small particles from drilling mud that stick to the cutting surface or in the surrounding fluid which can impact both mass measurements and NMR measurements. Washing may also benefit other subsequent measurements, such as gamma-ray measurement, on the drill cuttings because the effect of the small particles on the gamma ray measurements can be significant.

The figure on the left in FIG. 1, denoted A, illustrates a drill cuttings chip 10 with fluid 30 on the surface, with a volume of $V_{sur}$. The volume of the cutting inside the fluid envelope can be given as $V_c$. The figure on the right in FIG. 1, denoted B, is a magnified portion of the interior of the cutting chip 10 consisting of matrix grains 20 (may be in spheres or other geometric shapes) with volume of $V_m$ and density of $\rho_m$, and pore space 15, with volume of $V_c$ and filled by a fluid with a density of $\rho_l$.

Figure 2:
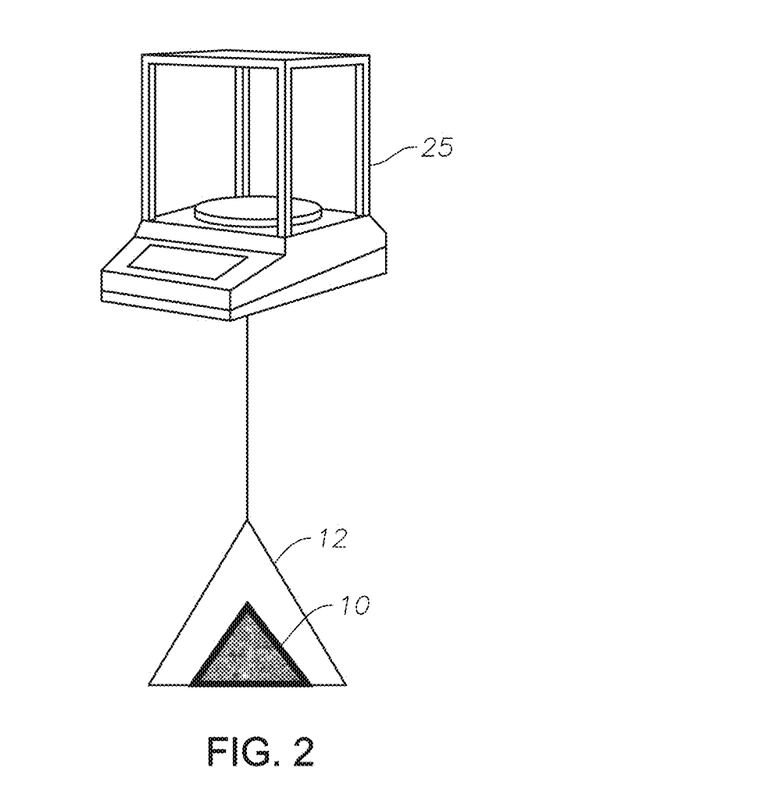
FIG. 2 illustrates an example apparatus for determining in-air mass of a fluid-saturated sample of a subsurface formation, according to one example embodiment of the disclosure.

The next step of the method is to measure the in-air mass of the collected drill cutting 10. FIG. 2, for example, illustrates an apparatus, such as a weighing balance 25 with a support device 12 that may be used to measure the in-air mass of the cutting sample 10. The in-air mass includes mass of the matrix or grains of the sample, mass of a fluid surrounding the sample, and mass of the fluid inside the sample. The in-air mass of the fluid-saturated sample, $m_s$, may be given by the formula $$m_s = V_m \rho_m + (V_\phi + V_{sur}) \rho_l$$

where $\rho_m$ is a density of the matrix of the subsurface formation, $\rho_l$ is a density of the fluid inside and surrounding the sample, $V_m$ is a volume of the matrix, $V_\phi$ is a volume of the fluid inside the sample, and $V_{sur}$ is a volume of the fluid surrounding the sample.

The next step is to separately determine volume of the fluid inside the sample, $V_\phi$, and volume of the fluid surrounding the sample, $V_{sur}$, using nuclear magnetic resonance (NMR). To clearly separate the NMR signals for liquid inside and surrounding the cuttings, a sufficient amount of surrounding fluid may be used one time or in a step-wise fashion. Due to the clay sensitivity issues, many wells in unconventional plays are drilled using oil based mud (OBM). The example embodiments disclosed propose a new method to separate the NMR signal of the fluid on the cuttings surfaces and the fluids from the interior pores of the cutting samples based on two assumptions: (1) fluids inside the shale cuttings have short relaxation time, and (2) fluid from OBM has a longer $T_2$, even in the presence of cuttings.

Figure 3:
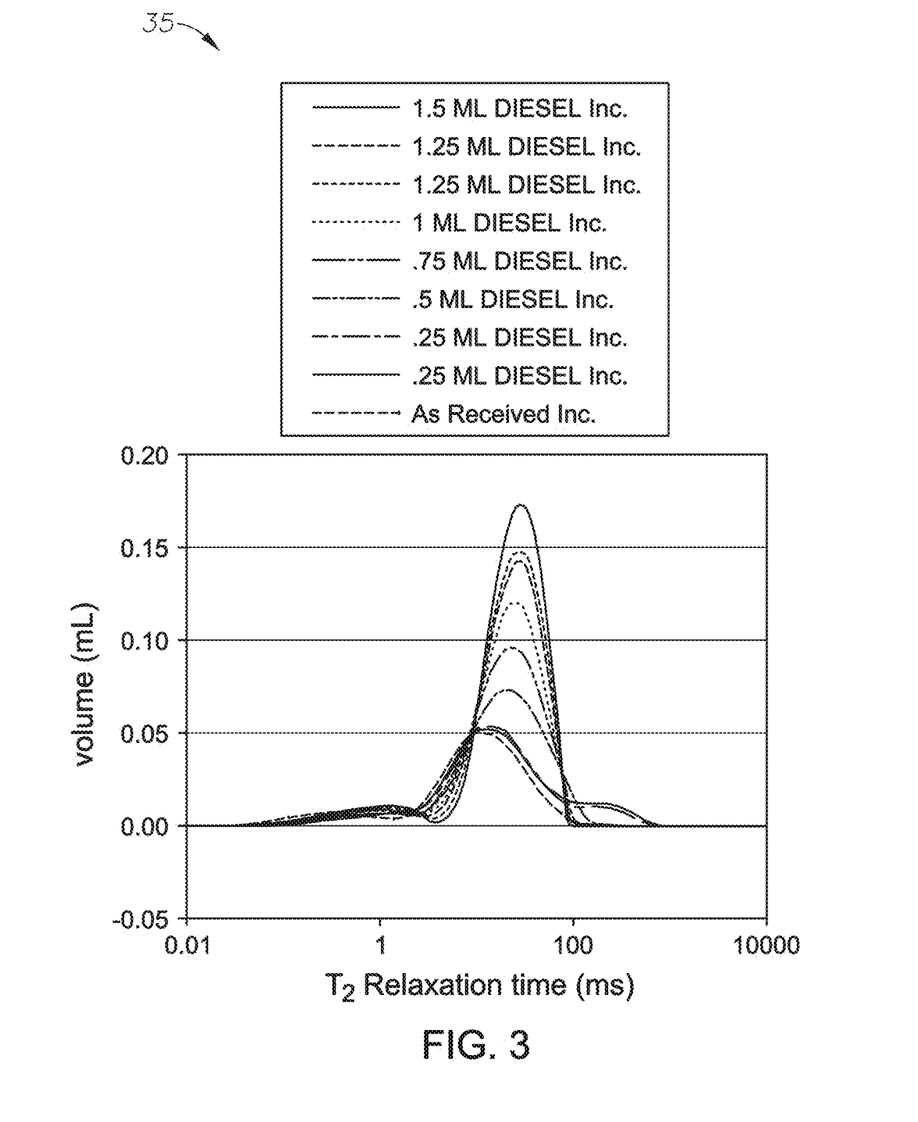
FIG. 3 illustrates example NMR spectra of a sample from a subsurface formation with varying amounts of washing fluid added, according to one example embodiment of the disclosure.

FIG. 3 illustrates an example graph 35 showing NMR readings (spectra) a sample of a subsurface formation with varying fluid content added to the sample, according to one example embodiment of the disclosure. A series of NMR experiments may be performed on the cutting sample and a $T_2$ incremental distribution spectra may be obtained as shown in FIG. 3, for example. A known amount of the drilling fluid, diesel for example, can be gradually added to the cutting sample and measurement may be made, e.g., "1.5 ML DIESEL Inc." stands for the incremental $T_2$ distribution curve after 1.5 ml diesel was added to the original cutting sample. Two modes of $T_2$ distribution may be noted, for example, a bigger one around 25 $m_s$ representing the free fluid, and a smaller peak below 1 $m_s$ representing the fluid inside the cutting samples.

A series of NMR experiments with cuttings demonstrate that the mode position of the $T_2$ signal of the OBM outside the cuttings does move to longer relaxation times as more fluid is gradually added (FIG. 3), and stops moving when the volume of added fluid is relatively large compared to the original amount of fluid on the surface. It should also be noted separation and quantification of the liquid inside the cuttings when a large amount of drilling fluid is present is attainable as there are two modes of $T_2$ distribution (FIG. 3). A larger peak around 25 $m_s$ representing the free fluid outside the cuttings, and a smaller peak below 1 $m_s$ representing the fluid inside the cutting samples. On the top curve (1.5 ml diesel inc., where the word 'inc.' stands for incremental $T_2$ distribution), the two modes are more clearly separated than the bottom curve (as received, i.e. no extra diesel is added).

Figure 4:
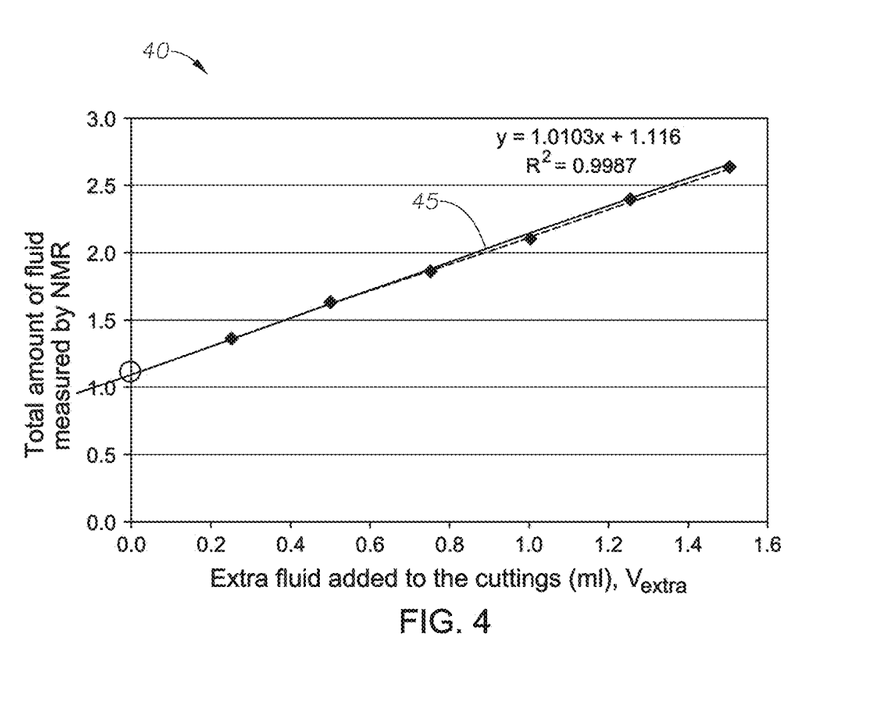
FIG. 4 illustrates an example graph showing NMR results of a sample of a subsurface formation, according to some example embodiments of the disclosure.
Figure 5:
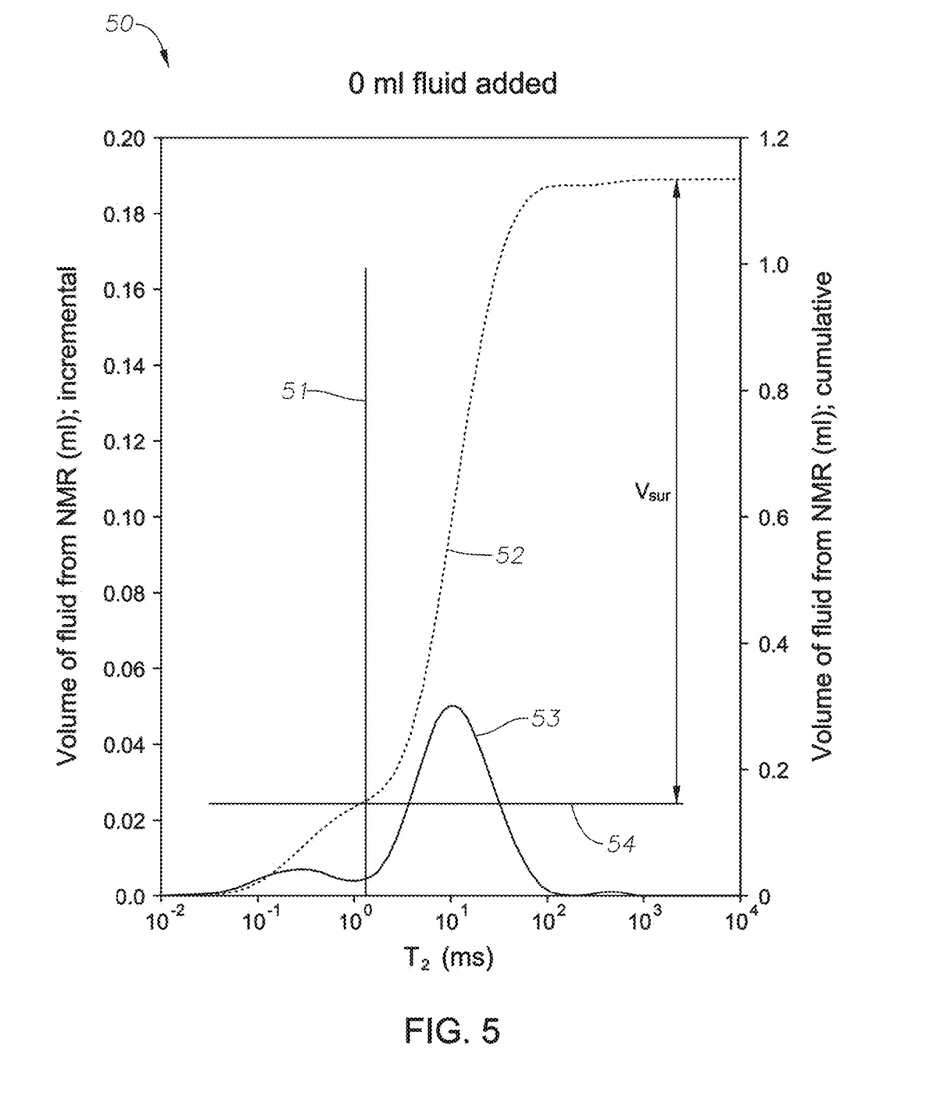
FIG. 5 illustrates example NMR spectra (one spectrum in incremental and the other in cumulative) of a sample from a subsurface formation without any extra fluid added, according to one example embodiment of the disclosure.

FIG. 4 illustrates an example graph 40 of the total amount of fluid measured by NMR (vertical axis) versus the extra fluid added to the cutting sample in ml (horizontal axis). It can be seen from the graph that line 45 intercepts with the vertical axis just above 1, and this is the total amount of fluid on the surface of and inside the cutting sample prior to the addition of diesel. FIG. 5 shows a graph 50 with no extra fluid added; a single point method of separation of $V_{sur}$ and Vp. Here it can be seen that the cumulative volume 52 of $T_2$ distribution of fluid from NMR measurement (scale on the right) and the incremental volume 53 of fluid (scale on the left) from NMR measurement are plotted.

No additional fluid is added in this variation of the method. A cut off 51 is selected from the incremental $T_2$ distribution line (a vertical dotted line drawn at the trough on the incremental curve in FIG. 5, the volume to the left of which represents the fluid volume inside the cuttings and to the right of which represents the volume on the surface, or bulk volume movable (BVM) when more fluid is added). The total volume of the fluid inside the cuttings (54, dashed line) can be read from the cumulative curve 52 and the volume on the surface of the cuttings is the difference between the total and the volume inside the cuttings ($V_{sur}$ in FIG. 5, or BVM on experiments when known amount of extra fluid is added)

Figure 6:
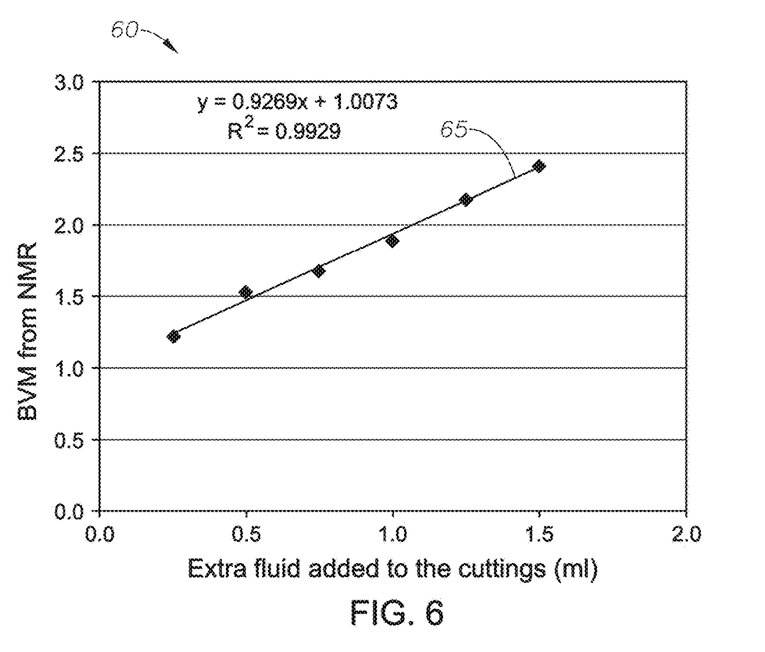
FIG. 6 illustrates an example graph showing NMR results of a sample of a subsurface formation, according to one example embodiment of the disclosure.

In case where excess fluid is present a plot can be graphed as seen in FIG. 6. Similar to line 45 shown in FIG. 4, line 65 in graph 60 shown in FIG. 6 illustrates that the BVM volume measurement from NMR increases as extra fluid is added to the cutting sample. Graph 60 shows a multi-point measurement from BVM to separate $V_{sur}$ and $V_\phi$, i.e. BVM vs. amounts of fluid added to the cutting sample. The intercept of the regression line 65 shows the volume of fluid on the surface of the cuttings ($V_{sur}$ is the intercept of the regression line, i.e. 1.0073 ml for this example).

Figure 7:
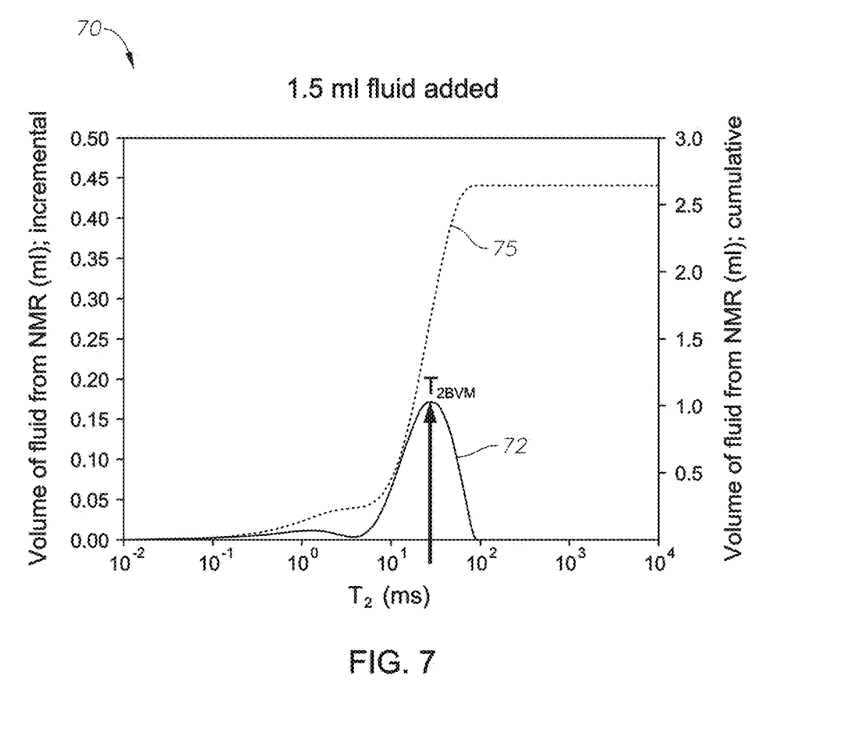
FIG. 7 illustrates an example of NMR results from a sample of a subsurface formation with extra fluid added (1.5 ml for this example), according to one example embodiment of the disclosure.
Figure 8:
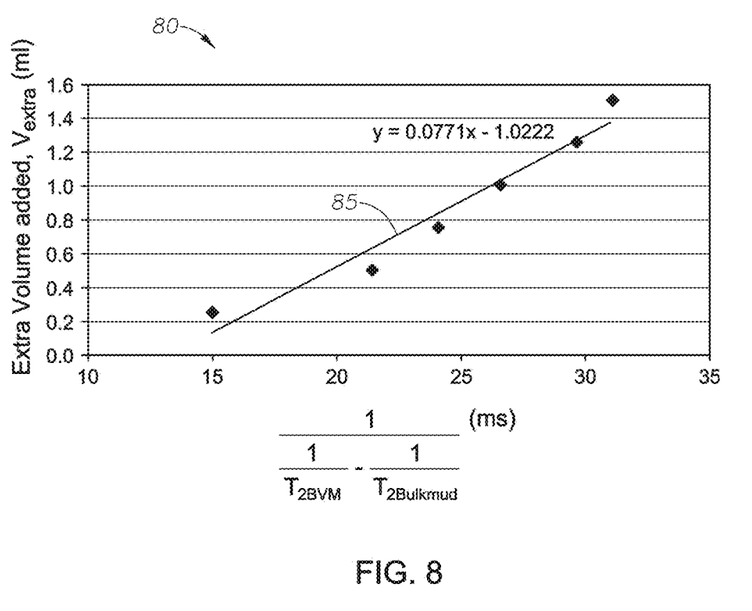
FIG. 8 illustrates an example graph showing NMR results from a sample of a subsurface formation, according to one example embodiment of the disclosure.

FIG. 7 illustrates another example graph 70 where 1.5 ml of fluid is added to the sample. Again both cumulative volume 75 of $T_2$ distribution (scale on the right) of fluid from NMR measurement and the incremental volume 72 (scale on the left) of $T_2$ distribution of fluid from NMR measurement are plotted. From the incremental volume 72 (scale on the left) of $T_2$ distribution curve, the mean of the bulk volume movable can be found, labeled as "$T_{2BVM}$". When various amounts of fluid are added to the sample, a series of "$T_{2BVM}$" values can be acquired in a method outlined here or other methods similar to the method outlined here, and the use of "$T_{2BVM}$" is shown in FIG. 8. Graph 80 shown in FIG. 8 illustrates a third way to get the amount of the fluid on the surface of cuttings, $V_{sur}$, using the $T_{2BVM}$ value. The negative of the intercept of the regression line 85 is the volume of fluid on the surface of the samples ($V_{sur}$ is the negative intercept of the regression line, i.e. 1.00222 ml for this example, where $T_{2bulkmud}$ is the $T_2$ relaxation time of the fluid (may be the drilling fluid or others) to rinse the sample with.

Figure 9:
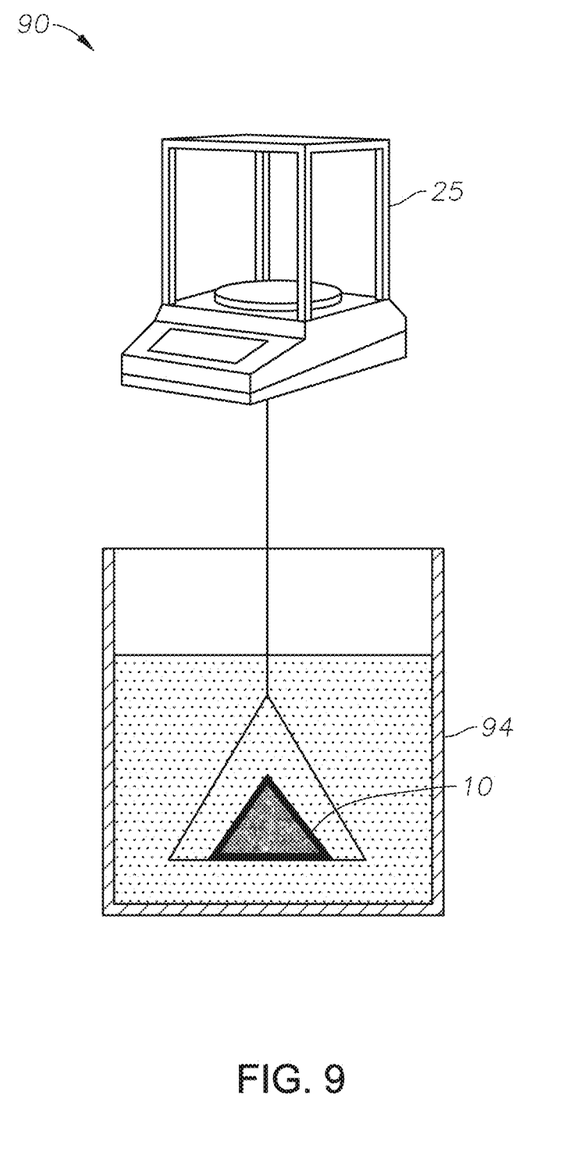
FIG. 9 illustrates an example apparatus for determining in-fluid mass of a fluid-saturated sample of a subsurface formation, according to some example embodiments of the disclosure.

The next step is to measure the sample mass in a weighing fluid. FIG. 9 illustrates an experimental set up 90 including an apparatus 25 for measuring the in-fluid mass of the sample, according to one example embodiment. In this example, the fluid-saturated sample 10 may be placed in a weighing fluid 94, and the weighing scale 25 may be used to measure the in-fluid mass of the sample 10. The weighing fluid can be the drilling fluid, or a fluid with gravimetric properties similar to the drilling fluid. In one example embodiment, the weighing fluid is diesel.

The mass of the sample in the weighing fluid, $m_f$, may be given by the formula $$m_f = V_m \rho_m + V_\phi \rho_l - V_c \rho_f$$

where $\rho_f$ is the density of the weighing fluid. From the combination of two mass measurements and NMR measurement, multiple key parameters can be obtained as outlined in the following sections for reservoir characterization. These parameters include porosity, cutting total volume, bulk density, and matrix/grain density. For example, the method may further include determining a volume of the fluid-saturated sample without the surrounding fluid, $V_c$, using the formula $$V_c = (m_s - m_f - V_{sur} \rho_l)/\rho_f.$$

In the next step, the method may also include determining a bulk density of the fluid-saturated sample without the surrounding fluid, $\rho_b$, using the formula $$\rho_b = \frac{V_m \rho_m + V_\phi \rho_l}{m_s - m_f - V_{sur} \rho_f} \rho_f.$$

In the next step, the method may further include determining the volume of the matrix, $V_m$, using the formula $$V_m = (m_s - m_f - V_{sur} \rho_f)/\rho_f - V_\phi.$$

As a last step, the method may include determining the matrix or grain density of the subsurface formation, $\rho_m$, using the formula $$\rho_m = \frac{m_s - (V_\phi + V_{sur})\rho_f}{(m_s - m_f - V_{sur}\rho_f)/\rho_f - V_\phi}.$$

These measurements can be performed on the cutting samples along the entirety of the drilled well and, thus, data can be obtained to evaluate the heterogeneity of the vertical or horizontal wells. This could potentially be used in real time to optimize the number and placement of frac stages for unconventional reservoirs.

Here, the contribution of the sample support device (12 in FIG. 1) is neglected, as the sample support device is chosen so the volume is minimum compared to the volume of the cuttings. There are three types of fluids involved in the drill cuttings analysis: the fluid inside the cutting samples, the drilling fluid, and the weighing fluid. At well site, depending on the permeability of the rock, the fluid inside can be replaced by the drilling fluid to various degrees. For example, for cuttings of unconventional rocks, it is likely that the fluid on the surface of the cuttings is different from the fluid inside, whereas for cuttings of very permeable rocks, the original fluid inside the cuttings is replaced by the drilling fluid rather quickly. If we choose the drilling fluid as the weighing liquid, the most complicated situation involves two types of fluids: the original fluid inside the pores and the drilling fluid. In the case where all three fluids are the same for high permeable rocks, the following calculations may be simplified even further. The following calculation uses two types of fluids as an example.

Figure 10:
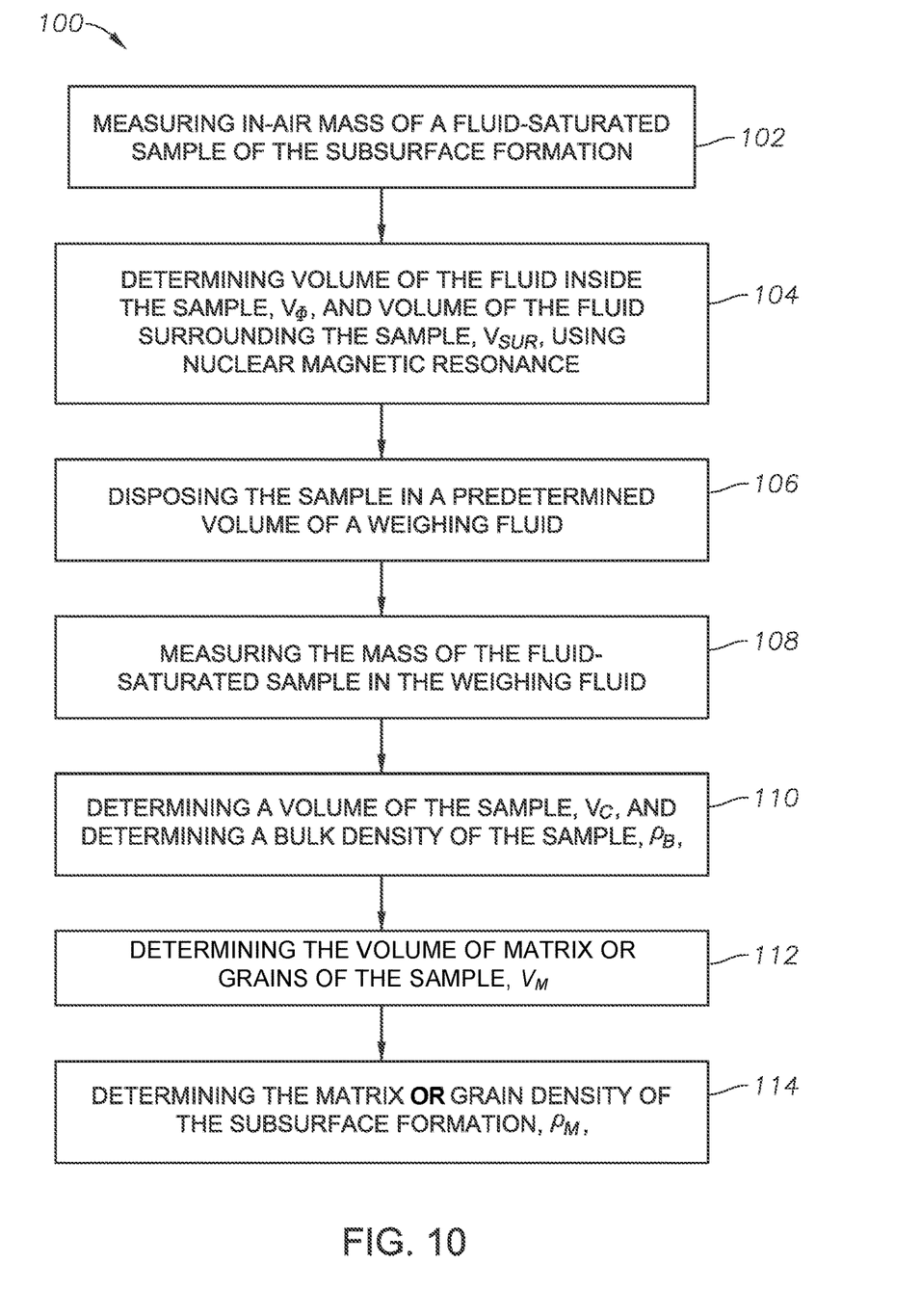
FIG. 10 illustrates example steps in a method for determining matrix or grain density of a subsurface formation, according to some example embodiments of the disclosure.

FIG. 10 illustrates an example method 100 for determining matrix or grain density of a subsurface formation. The method includes measuring in-air mass of a fluid-saturated sample of the subsurface formation in step 102, wherein the in-air mass includes mass of the matrix or grains of the sample, mass of a fluid surrounding the sample, and mass of the fluid inside the sample. The in-air mass of the fluid-saturated sample, $m_s$, may be given by the formula $$m_s = V_m \rho_m + (V_\phi + V_{sur})\rho_l$$

where $\rho_m$ is a density of the matrix of the subsurface formation, $\rho_l$ is a density of the fluid inside and surrounding the sample, $V_m$ is a volume of the matrix, $V_\phi$ is a volume of the fluid inside the sample, and $V_{sur}$ is a volume of the fluid surrounding the sample. The method also includes separately determining volume of the fluid inside the sample, $V_\phi$, and volume of the fluid surrounding the sample, $V_{sur}$, using nuclear magnetic resonance (NMR), at step 104. The method may further include placing the sample in a predetermined volume of a weighing fluid at step 106, and measuring the mass of the fluid-saturated sample in the weighing fluid, at step 108. The mass of the fluid-saturated sample without the surrounding fluid in the weighing fluid, $m_f$, may be given by the formula $$m_f = V_m \rho_m + V_\phi \rho_l - V_c \rho_f$$

where $\rho_f$ is the density of the weighing fluid. At step 110, the method may further include determining a volume of the fluid-saturated sample without the surrounding fluid, $V_c$, using the formula $$V_c = (m_s - m_f - V_{sur}\rho_l)/\rho_f.$$

The method may also include determining a bulk density of the fluid-saturated sample without the surrounding fluid, $\rho_b$, using the formula $$\rho_b = \frac{V_m\rho_m + V_\phi\rho_l}{m_s - m_f - V_{sur}\rho_f}\rho_f.$$

At step 112, the method may further include determining the volume of the matrix, $V_m$, using the formula $$V_m = (m_s - m_f - V_{sur}\rho_f)/\rho_f - V_\phi.$$

Finally, at step 114, the method may include determining the matrix or grain density of the subsurface formation, $\rho_m$, using the formula $$\rho_m = \frac{m_s - (V_\phi + V_{sur})\rho_f}{(m_s - m_f - V_{sur}\rho_f)/\rho_f - V_\phi}.$$

Computer Readable Medium

Figure 11:
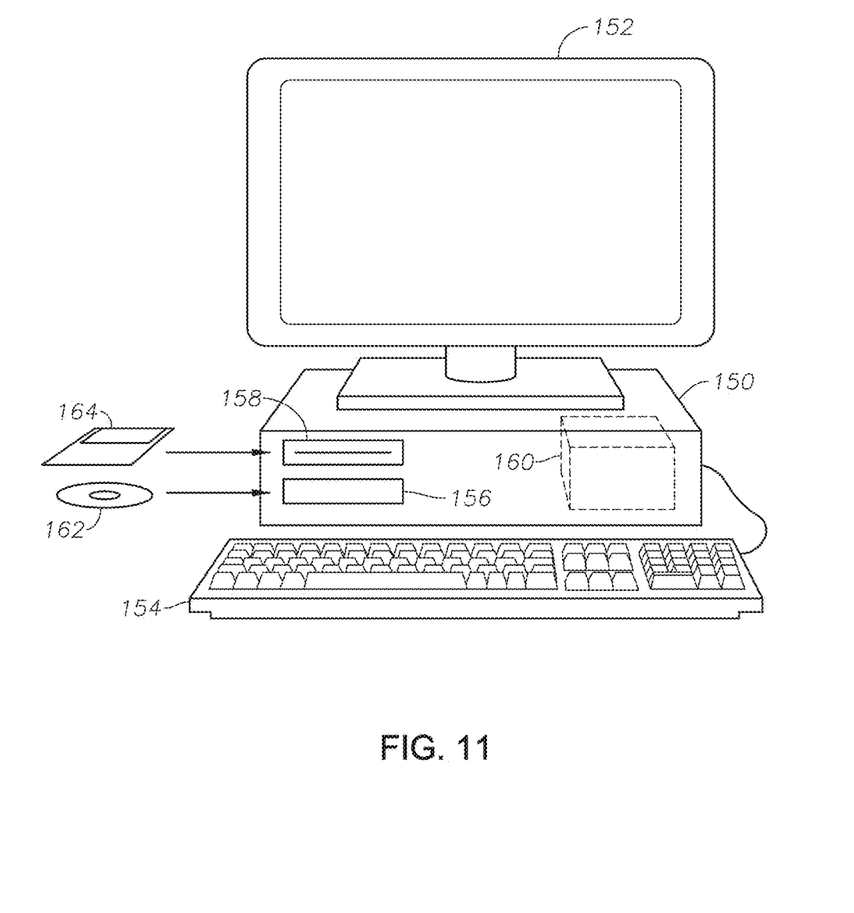
FIG. 11 is an example computer set up for determining matrix or grain density of a subsurface formation, according to some example embodiments of the disclosure.
Figure 12:
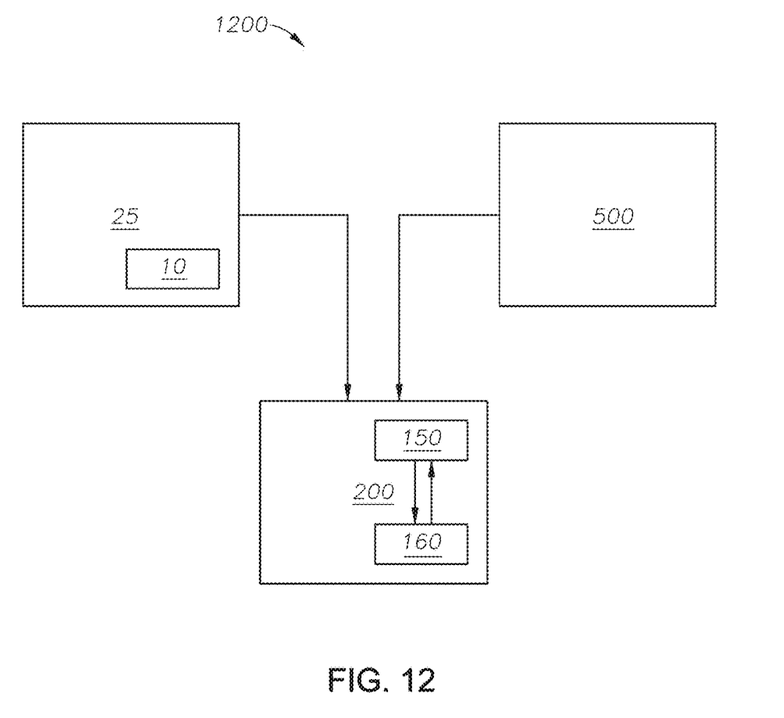
FIG. 12 is an example system for determining matrix or grain density of a subsurface formation, according to some example embodiments of the disclosure.

Another example embodiment relates to computer programs stored in computer readable media. Referring to FIG. 11, the foregoing process as explained with reference to FIGS. 1-10 can be embodied in computer-readable code. The code can be stored on, e.g., a non-transitory computer readable medium, such as a floppy disk 164, CD-ROM 162, which may be read by disk drives 156, 158, or a magnetic (or other type) hard drive 160 forming part of a general purpose programmable computer. The computer, as known in the art, includes a central processing unit 150, a user input device such as a keyboard 154, and a user display 152 such as a flat panel LCD display or cathode ray tube display. According to this embodiment, the computer readable medium 160, 162, 164 includes logic operable to trigger the computer to execute acts as set forth above and explained with respect to the previous figures. The non-transitory computer-readable medium 160, 162, 164 may have, for example, computer executable instructions that trigger the computer to perform the operations of receiving in-air mass of a fluid-saturated sample of the subsurface formation, wherein the in-air mass includes mass of the matrix or grains of the sample, mass of a fluid surrounding the sample, and mass of the fluid inside the sample. The in-air mass of the fluid-saturated sample, $m_s$, may be given by the formula $$m_s = V_m\rho_m + (V_\phi + V_{sur})\rho_l$$

where $\rho_m$ is a density of the matrix of the subsurface formation, $\rho_l$ is a density of the fluid inside and surrounding the sample, $V_m$ is a volume of the matrix, $V_\phi$ is a volume of the fluid inside the sample, and $V_{sur}$ is a volume of the fluid surrounding the sample. The computer executable instructions may also trigger the computer to determine volume of the fluid inside the sample, $V_\phi$, and volume of the fluid surrounding the sample, $V_{sur}$, using nuclear magnetic resonance (NMR). The computer executable instructions may also trigger the computer to receive mass of the fluid-saturated sample in a weighing fluid. The mass of the fluid-saturated sample without the surrounding fluid in the weighing fluid, $m_f$, may be given by the formula $$m_f = V_m\rho_m + V_\phi\rho_l - V_c\rho_f$$

where $\rho_f$ is the density of the weighing fluid. The computer executable instructions may also trigger the computer to determine a volume of the sample without the surrounding fluid, $V_c$, using the formula $$V_c = (m_s - m_f - V_{sur}\rho_l)/\rho_f.$$

The computer executable instructions may further trigger the computer to determine a bulk density of the fluid-saturated sample without the surrounding fluid, $\rho_b$, using the formula $$\rho_b = \frac{V_m\rho_m + V_\phi\rho_l}{m_s - m_f - V_{sur}\rho_f}\rho_f.$$

The computer executable instructions may further trigger the computer to determine the volume of the matrix, $V_m$, using the formula $$V_m = (m_s - m_f - V_{sur}\rho_f)/\rho_f - V_\phi.$$

The computer executable instructions may further trigger the computer to determine the matrix or grain density of the subsurface formation, $\rho_m$, using the formula $$\rho_m = \frac{m_s - (V_\phi + V_{sur})\rho_f}{(m_s - m_f - V_{sur}\rho_f)/\rho_f - V_\phi}.$$

Example System

Another example embodiment is a system 1200 for determining matrix or grain density of a subsurface formation. The system 1200 may include a fluid-saturated sample 10 of the subsurface formation, as illustrated in FIGS. 1, 2, and 9. The system 1200 may also include a weighing scale 25, as illustrated in FIGS. 2 and 9, which may be configured to receive the fluid-saturated sample 10 and output the in-air mass and in-fluid mass of the sample 10. The system 1200 may also include a computer 200 having one or more processors 150 and a non-transitory computer readable medium 160, which may include computer executable instructions that when executed by the one or more processors 150, trigger the computer 200 to receive in-air mass of the fluid-saturated sample 10 of the subsurface formation from the weighing scale 25. The in-air mass may include mass of the matrix or grains of the sample, mass of a fluid surrounding the sample, and mass of the fluid inside the sample. The in-air mass of the fluid-saturated sample, $m_s$, may be given by the formula $$m_s = V_m\rho_m + (V_\phi + V_{sur})\rho_l$$

where $\rho_m$ is a density of the matrix of the subsurface formation, $\rho_l$ is a density of the fluid inside and surrounding the sample, $V_m$ is a volume of the matrix, $V_\phi$ is a volume of the fluid inside the sample, and $V_{sur}$ is a volume of the fluid surrounding the sample. The system 1200 may also include a NMR device 500, which may be operably connected to computer 200 and configured to determine the volume of the fluid inside the sample, $V_\phi$, and volume of the fluid surrounding the sample, $V_{sur}$, using nuclear magnetic resonance (NMR). The computer 200 may be configured to receive the volume of the fluid inside the sample, $V_\phi$, and volume of the fluid surrounding the sample, $V_c$, from the NMR device 500, and the mass of the fluid-saturated sample in a weighing fluid from the weighing scale 25. The mass of the fluid-saturated sample without the surrounding fluid in the weighing fluid, $M_f$, may be given by the formula $$m_f = V_m\rho_m + V_\phi\rho_l - V_c\rho_f$$

where $\rho_f$ is the density of the weighing fluid. The computer executable instructions may also trigger the computer to determine a volume of the fluid-saturated sample without the surrounding fluid, $V_c$, using the formula $$V_c=(m_s-m_f-V_{sur}\rho_l)/\rho_f$$

The computer executable instructions may further trigger the computer to determine a bulk density of the fluid-saturated sample without the surrounding fluid, $\rho_b$, using the formula $$\rho_b = \frac{V_m\rho_m + V_\phi\rho_l}{m_s - m_f - V_{sur}\rho_f}\rho_f.$$

The computer executable instructions may further trigger the computer to determine the volume of the matrix, $V_m$, using the formula $$V_m=(m_s-m_f-V_{sur}\rho_f)/\rho_f-V_\phi.$$

The computer executable instructions may further trigger the computer to determine the matrix or grain density of the subsurface formation, $\rho_m$, using the formula $$\rho_m = \frac{m_s - (V_\phi + V_{sur})\rho_f}{(m_s - m_f - V_{sur}\rho_f)/\rho_f - V_\phi}.$$

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

The invention claimed is:

1. A method for characterization of a subsurface formation, the method comprising:

measuring in-air mass of a fluid-saturated sample of the subsurface formation, wherein the in-air mass comprises mass of matrix or grains of the sample, mass of a fluid surrounding the sample, and mass of the fluid inside the sample, the in-air mass of the fluid-saturated sample, $m_s$, given by the formula:

$$m_s=V_m\rho_m+(V_\phi+V_{sur})\rho_l$$

where $\rho_m$ is a density of the matrix of the subsurface formation, $\rho_l$ is a density of the fluid inside and surrounding the sample, $V_m$ is a volume of the matrix, $V_\phi$ is a volume of the fluid inside the sample, and $V_{sur}$ is a volume of the fluid surrounding the sample;

determining volume of the fluid inside the sample, $V_\phi$, and volume of the fluid surrounding the sample, $V_{sur}$, using nuclear magnetic resonance (NMR);

placing the fluid-saturated sample in a predetermined volume of a weighing fluid;

measuring mass of the fluid-saturated sample in the weighing fluid;

determining mass of the fluid-saturated sample without the surrounding fluid in the weighing fluid, $m_f$, given by the formula:

$$m_f=V_m\rho_m+V_\phi\rho_l-V_c\rho_f$$

where $\rho_f$ is the density of the weighing fluid; and determining a volume of the fluid-saturated sample without the surrounding fluid, $V_c$, using the formula:

$$V_c=(m_s-m_f-V_{sur}\rho_l)/\rho_f$$

2. The method of claim 1, further comprising:

determining a bulk density of the fluid-saturated sample without the surrounding fluid, p, using the formula:

$$\rho_b = \frac{V_m\rho_m + V_\phi\rho_l}{m_s - m_f - V_{sur}\rho_f}\rho_f.$$

3. The method of claim 2, further comprising:

determining volume of the matrix, $V_m$, using the formula:

$$V_m=(m_s-m_f-V_{sur}\rho_f)/\rho_f-V_\phi.$$

4. The method of claim 3, further comprising:

determining matrix or grain density of the subsurface formation, $\rho_m$, using the formula:

$$\rho_m = \frac{m_s - (V_\phi + V_{sur})\rho_f}{(m_s - m_f - V_{sur}\rho_f)/\rho_f - V_\phi}.$$

5. The method of claim 1, further comprising:

washing the sample using a washing fluid prior to measuring, wherein the washing fluid is same as a drilling fluid.

6. The method of claim 1, wherein at least one dimension of the fluid-saturated sample is about 0.5 mm to 3 mm.

7. The method of claim 1, wherein the weighing fluid is a drilling fluid, or a fluid with gravimetric properties similar to the drilling fluid.

8. The method of claim 1, wherein the weighing fluid is diesel.

9. The method of claim 1, wherein the fluid-saturated sample does not require physical removal of the surrounding fluid.

* * * * *